United States Patent
Shan et al.

(10) Patent No.: US 12,359,985 B2
(45) Date of Patent: Jul. 15, 2025

(54) TRANSDUCTION UNIT OF NON-CONTACT HUMAN SLEEP PHYSIOLOGICAL PARAMETER DETECTION SENSOR

(71) Applicants: Keeson Technology Corporation Limited, Zhejiang (CN); Yangtze Delta Region Institute of Tsinghua University, Zhejiang, Zhejiang (CN)

(72) Inventors: Huafeng Shan, Zhejiang (CN); Kaimin Cao, Zhejiang (CN); Jiadong Wang, Zhejiang (CN); Hongwen Li, Zhejiang (CN); Xiuping Han, Zhejiang (CN); Xin Jin, Zhejiang (CN)

(73) Assignees: Keeson Technology Corporation Limited, Jiaxing (CN); Yangtze Delta Region Institute of Tsinghua University, Zhejiang, Jiaxing (CN)

( * ) Notice: Subject to any disclaimer, the term of this patent is extended or adjusted under 35 U.S.C. 154(b) by 361 days.

(21) Appl. No.: 17/908,910

(22) PCT Filed: Mar. 2, 2021

(86) PCT No.: PCT/CN2021/078590
§ 371 (c)(1),
(2) Date: Sep. 1, 2022

(87) PCT Pub. No.: WO2021/190255
PCT Pub. Date: Sep. 30, 2021

(65) Prior Publication Data
US 2023/0088408 A1    Mar. 23, 2023

(30) Foreign Application Priority Data
Mar. 25, 2020 (CN) .......................... 202010216305.1

(51) Int. Cl.
*G01L 1/16* (2006.01)
*A61B 5/00* (2006.01)
(Continued)

(52) U.S. Cl.
CPC .............. *G01L 1/16* (2013.01); *A61B 5/4806* (2013.01); *H10N 30/302* (2023.02); *H10N 30/875* (2023.02); *H10N 30/883* (2023.02)

(58) Field of Classification Search
CPC ....................................................... G01L 1/16
See application file for complete search history.

(56) References Cited

U.S. PATENT DOCUMENTS

| 6,141,844 A | 11/2000 | Miyagawa et al. |
| 2003/0045806 A1 | 3/2003 | Brydon |

FOREIGN PATENT DOCUMENTS

| CN | 103674225 A | 3/2014 |
| CN | 102157678 B | 7/2015 |

(Continued)

OTHER PUBLICATIONS

Partial supplementary search report of counterpart European Patent Application No. 21775886.1 issued on Mar. 28, 2024.
(Continued)

*Primary Examiner* — Walter L Lindsay, Jr.
*Assistant Examiner* — Andrew V Do (57) ABSTRACT

A transduction unit of a non-contact human sleep physiological parameter detection sensor includes a circuit board, a piezoelectric film and conductive adhesives, wherein the piezoelectric film includes a film sheet and two electrodes, which are respectively arranged on two side faces of the film sheet; the piezoelectric film is attached to the circuit board; and the two electrodes of the piezoelectric film are respectively electrically connected to two exposed pad electrodes on the circuit board by means of the conductive adhesives.

7 Claims, 8 Drawing Sheets

(51) Int. Cl.
*H10N 30/30* (2023.01)
*H10N 30/87* (2023.01)
*H10N 30/88* (2023.01)

(56) References Cited

FOREIGN PATENT DOCUMENTS

| CN | 106725338 A | 5/2017 | |
|---|---|---|---|
| CN | 107526435 A | 12/2017 | |
| CN | 109668952 A | 4/2019 | |
| CN | 211376665 U | 8/2020 | |
| WO | WO-2015041049 A1 * | 3/2015 | ............. H01L 41/04 |

OTHER PUBLICATIONS

International search report of PCT Patent Application No. PCT/CN2021/078590 issued on May 28, 2021.

* cited by examiner

TRANSDUCTION UNIT OF NON-CONTACT HUMAN SLEEP PHYSIOLOGICAL PARAMETER DETECTION SENSOR

FIELD OF THE INVENTION

The present disclosure relates to the technical field of piezoelectric films, and in particular to a transduction unit of a non-contact human sleep physiological parameter detection sensor.

BACKGROUND OF THE INVENTION

An existing transduction unit is commonly made of piezoelectric ceramics. By a structural design, a variable force necessary to be detected is loaded onto the piezoelectric ceramics, and the piezoelectric ceramics converts the force into an electrical signal. Compared with the piezoelectric ceramics, the piezoelectric film has a lower relative dielectric constant. Although having a piezoelectric strain constant less than that of the piezoelectric ceramics, the piezoelectric film has characteristics of a higher piezoelectric voltage constant, a wide band response range, high impact strength, etc., and would be easily cut and machined.

However, in the existing piezoelectric film, for example, a piezoelectric film element disclosed in the invention patent No. ZL201110023507.5, it is necessary to connect two electrodes of the piezoelectric film to a voltage detection apparatus via leads; moreover, a jig is required for fixing the piezoelectric film, and thus the overall structure is complicated, the volume is increased, which is not conducive to assembling the piezoelectric film on some detection devices, and the electromechanical conversion efficiency is degraded due to the complexity of voltage signal conduction pathways.

SUMMARY OF THE INVENTION

In order to solve the above problems in the existing techniques, an objective of the disclosure is to propose a transduction unit of a non-contact human sleep physiological parameter detection sensor, which has a simple structure, is easily assembled and produced on a large scale, and also has high electromechanical conversion efficiency.

The objective of the disclosure is realized by the following solutions.

A transduction unit of a non-contact human sleep physiological parameter detection sensor includes a circuit board, a piezoelectric film and conductive adhesives. The piezoelectric film includes a film sheet and two electrodes, which are respectively arranged on two side faces of the film sheet. The piezoelectric film is attached to the circuit board. The two electrodes of the piezoelectric film are respectively electrically connected to two exposed pad electrodes on the circuit board via the conductive adhesives.

In the disclosure, the piezoelectric film is attached to the circuit board generally by using the conductive adhesives, the piezoelectric film is also connected to the electrodes of the circuit board via the conductive adhesives, and a voltage signal is directly transmitted to a processing circuit on the circuit board through the conductive adhesives for processing. The disclosed structure is greatly simplified, leading to a wider range of applications, and thus can be easily assembled and produced on a large scale. In the meanwhile, the solution can also realize high electromechanical conversion efficiency and a more accurate conversion result. It should be noted that the circuit board in the solution can be a rigid circuit board, for example, a conventional PCB taking FR4 as a base material. The conventional rigid circuit board itself also has a certain magnitude of deformation, which can satisfy a sensing range of the piezoelectric film, and the cost of the rigid circuit board is lower. Certainly, the solution is also applicable to a flexible circuit board.

As a preferred embodiment, one of the electrodes of the piezoelectric film that faces towards the circuit board is connected to one of the exposed pad electrodes on the circuit board via one of the conductive adhesives. One of the side faces of the film sheet that faces towards the circuit board is further provided with a transfer electrode. Another of the conductive adhesives is connected, at its one end, to the transfer electrode and another of the exposed pad electrodes on the circuit board, and is folded, at its opposite end, to another of the side faces of the film sheet around an edge of the film sheet, so as to be connected to the electrode on this another side face.

As a preferred embodiment, the one conductive adhesive is a three-direction conductive adhesive or a z-direction conductive adhesive, and the another conductive adhesive is a three-direction conductive adhesive.

As a preferred embodiment, the circuit board has a length greater than that of the piezoelectric film. One of the exposed pad electrodes on the circuit board is arranged outside a coverage face of the piezoelectric film. One of the conductive adhesives is connected, with its two side faces, to the electrode of the piezoelectric film that faces towards the circuit board and one of the exposed pad electrodes on the circuit board, and another of the conductive adhesives is connected, with a same side face, to another electrode of the piezoelectric film that faces away from the circuit board and another of the exposed pad electrodes on the circuit board.

As a preferred embodiment, the one conductive adhesive is a three-direction conductive adhesive or a z-direction conductive adhesive, and the another conductive adhesive is a three-direction conductive adhesive.

As a preferred embodiment, the side face of the film sheet that faces towards the circuit board is further provided with an extension electrode. A through hole penetrates the electrode of the piezoelectric film that faces away from the circuit board, the film sheet and the extension electrode. The extension electrode is connected, through the through hole, to the electrode of the piezoelectric film on a side facing away from the circuit board. The electrode of the piezoelectric film that faces towards the circuit board and the extension electrode are respectively connected to the two exposed pad electrodes on the circuit board via the conductive adhesives.

As a preferred embodiment, the conductive adhesives are formed as one z-direction conductive adhesive, or two z-direction conductive adhesives or three-direction conductive adhesives, which are separated from each other.

As a preferred embodiment, the side of the piezoelectric film that faces away from the circuit board is further provided with a protective film.

The disclosure has advantages of being simple in structure, wide in application, convenient in assemble and mass production, efficient in electromechanical conversion, and accurate in conversion results.

1—Circuit board; 2—Piezoelectric film; 3, 31, 32—Conductive adhesive; 11—Negative electrode of the circuit board; 12—Positive electrode of the circuit board; 21—Film sheet; 22—Positive electrode of the piezoelectric film; 23—Negative electrode of the piezoelectric film; 24—Transfer electrode; 25—Extension electrode; 211—Through hole.

DETAILED DESCRIPTION OF THE EMBODIMENTS

The disclosure is further described below in detail in conjunction with the accompanying drawings and the particular implementations.

Embodiment I

Figure 1:
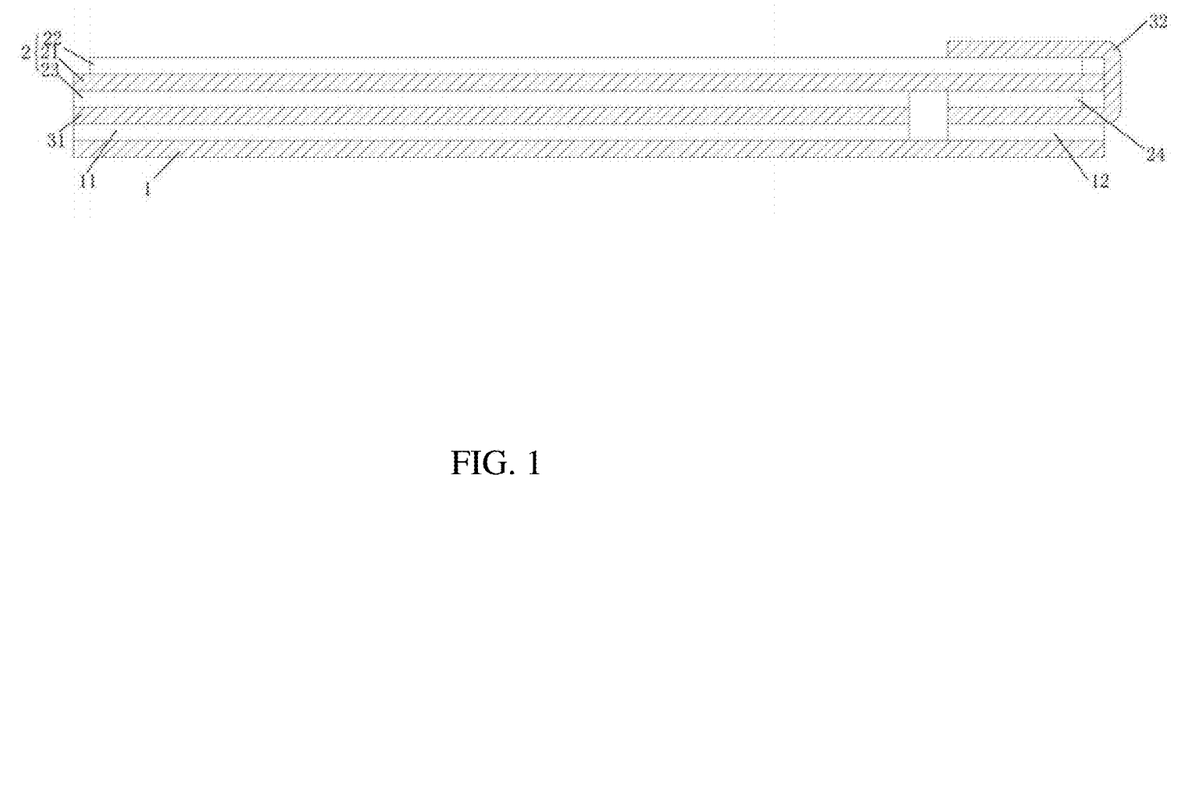
FIG. 1 is a schematic structural diagram of Embodiment I of the disclosure.
Figure 2:
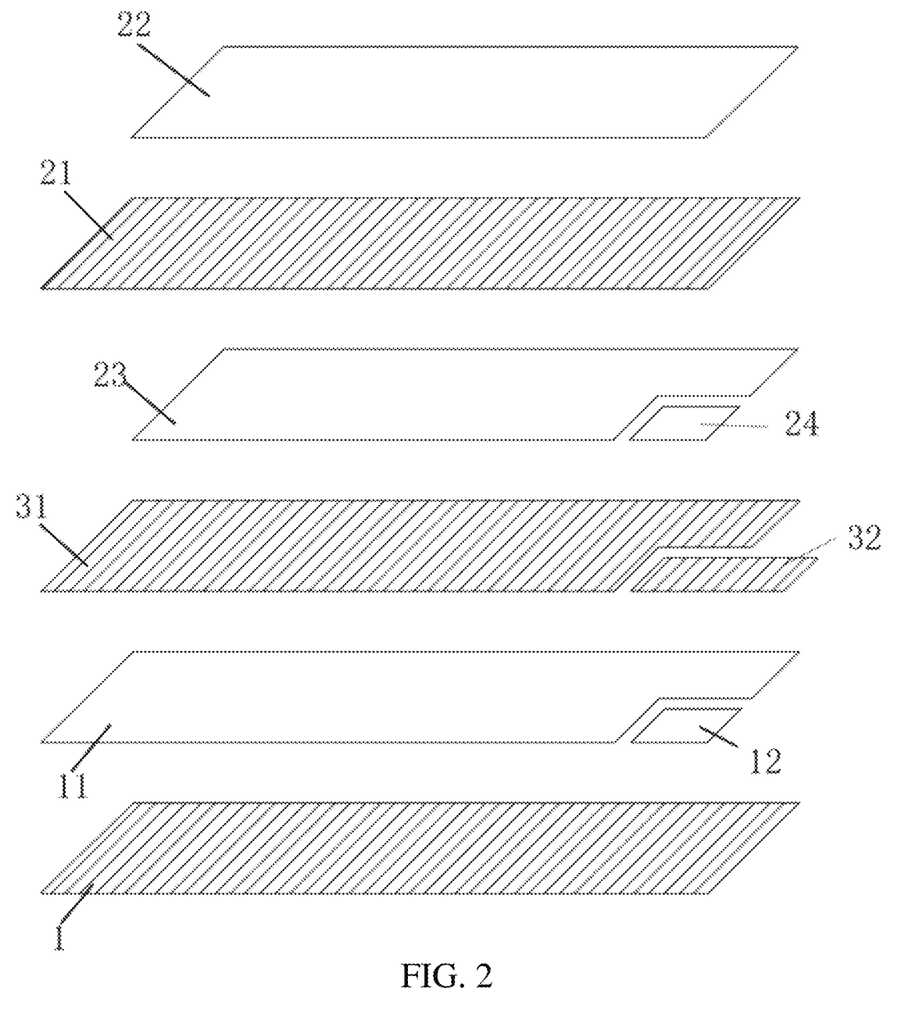
FIG. 2 is a schematic exploded structural diagram of the Embodiment I of the disclosure.

As shown in FIGS. 1-2, a transduction unit of a non-contact human sleep physiological parameter detection sensor includes a piezoelectric film 2, a circuit board 1, which is provided with exposed pad electrodes matching the piezoelectric film, and conductive adhesives. The piezoelectric film 2 includes a film sheet 21 and two electrodes, which are respectively arranged on two side faces of the film sheet 21. The two electrodes cannot both extend to an edge from a same end on the film sheet, so as to prevent the two electrodes from coming into contact at the edge of the film sheet and causing a short circuit. The exposed pad electrodes each adopt a plating with good conductivity and oxidation resistance, and can be manufactured in a leveling process, such as a metal deposition process. The piezoelectric film 2 is attached to the circuit board 1. The two electrodes of the piezoelectric film 2 are respectively connected to the two electrodes on the circuit board 1 via the conductive adhesives. The circuit board 1 can be a rigid circuit board, for example, a conventional PCB taking FR4 as a base material. The conventional rigid circuit board itself also has a certain magnitude of deformation, which can satisfy a sensing range of the piezoelectric film, and the cost of the rigid circuit board is lower. Certainly, the embodiment is also applicable to a flexible circuit board.

In particular, description is made by taking a top side face (as shown in the figures) of the film sheet 21 as a positive electrode 22 of the piezoelectric film, a bottom side face (as shown in the figures) thereof as a negative electrode 23 of the piezoelectric film, one of the exposed pad electrodes on the circuit board 1 that has larger area as a negative electrode 11 of the circuit board, and one of the exposed pad electrodes on the circuit board 1 that has smaller area as a positive electrode 12 of the circuit board.

The negative electrode 23 of the piezoelectric film does not cover the entire bottom side face of the film sheet 21, has a shape corresponding to that of the negative electrode 11 of the circuit board, and is bonded thereto via one three-direction conductive adhesive or z-direction conductive adhesive that has a corresponding shape. A part of the bottom side face of the film sheet 21 that is not covered by the negative electrode 23 of the piezoelectric film is provided with a transfer electrode 24. The transfer electrode 24 has a shape corresponding to that of the positive electrode 12 of the circuit board, and is bonded thereto via one three-direction conductive adhesive 32, the length of which is greater than that of the transfer electrode 24. A part of the conductive adhesive that extends out of the film sheet 21 is folded upwards to be bonded to the positive electrode 22 of the piezoelectric film on the top side face of the film sheet, so as to complete the bonding of the entire piezoelectric film 2 and the circuit board 1, and an electrical connection between their electrodes.

In addition, in order to facilitate the folding of the conductive adhesive, the conductive adhesive 32 is of a structure having a smaller width, i.e., a width that cannot cover most of the circuit board 1 and the piezoelectric film 2. Correspondingly, the positive electrode 12 of the circuit board and the transfer electrode 24 also each have a width corresponding to that of the conductive adhesive. Hence, in order to ensure the bonding area and the bonding strength between the piezoelectric film 2 and the circuit board 1, the negative electrode 11 of the circuit board extends to one side of the positive electrode 12 of the circuit board, and the negative electrode 23 of the piezoelectric film extends to one side of the transfer electrode 24, so as to increase the coverage area with respect to the circuit board 1 and the piezoelectric film 2, that is, to increase the coverage area of the conductive adhesive with respect to the circuit board 1 and the piezoelectric film 2, thereby improving the bonding strength between the circuit board 1 and the piezoelectric film 2, and improving sensing accuracy of the piezoelectric film.

Finally, in order to protect the piezoelectric film, one protective film is generally provided on the top side face of the piezoelectric film.

Embodiment II

Figure 3:
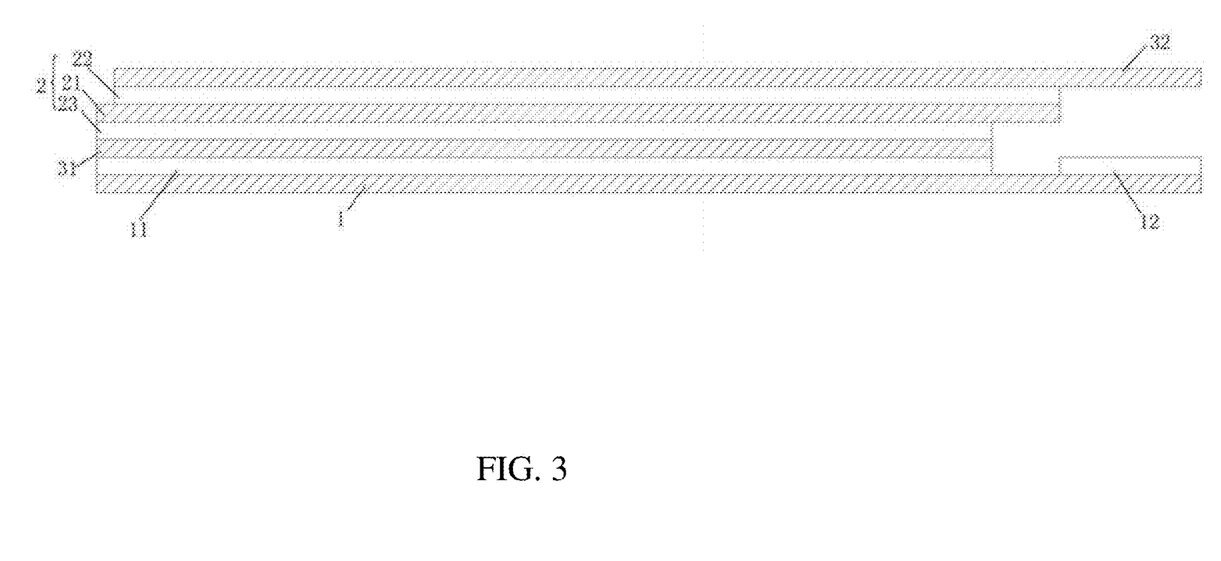
FIG. 3 is a schematic structural diagram of Embodiment II of the disclosure.
Figure 4:
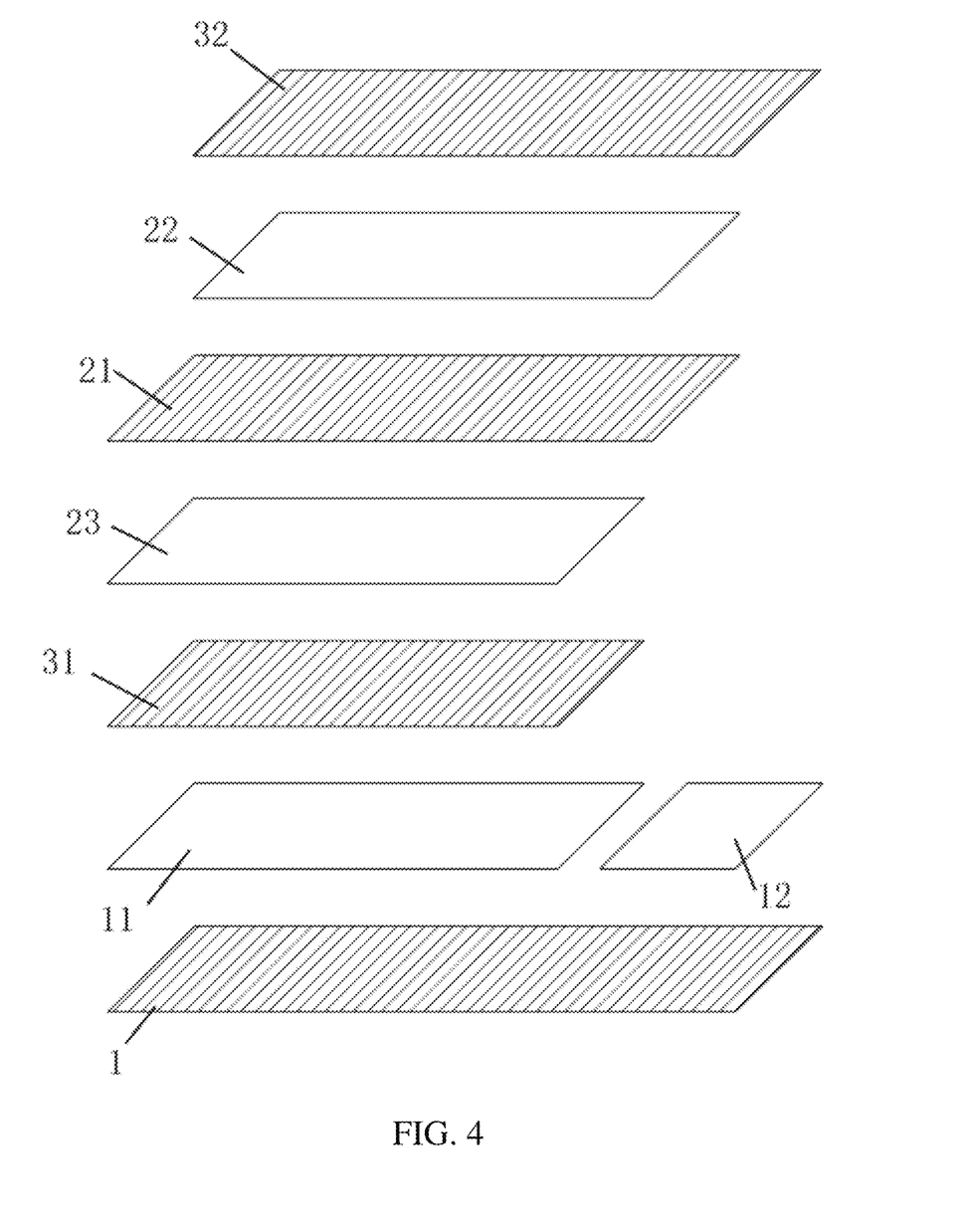
FIG. 4 is a schematic exploded structural diagram of the Embodiment II of the disclosure.

As shown in FIGS. 3-4, a transduction unit of a non-contact human sleep physiological parameter detection sensor includes a piezoelectric film 2, a circuit board 1, which is provided with exposed pad electrodes matching the piezoelectric film, and conductive adhesives. The piezoelectric film 2 includes a film sheet 21 and two electrodes, which are respectively arranged on two side faces of the film sheet 21. The two electrodes cannot both extend to an edge from a same end on the film sheet, so as to prevent the two electrodes from coming into contact at the edge of the film sheet and causing a short circuit. The exposed pad electrodes each adopt a plating with good conductivity and oxidation resistance, and can be manufactured in a leveling process, such as a metal deposition process. The piezoelectric film 2 is attached to the circuit board 1. The two electrodes of the piezoelectric film 2 are respectively connected to the two electrodes on the circuit board 1 via the conductive adhesives. The circuit board 1 can be a rigid circuit board, for example, a conventional PCB taking FR4 as a base material. The conventional rigid circuit board itself also has a certain magnitude of deformation, which can satisfy a sensing range of the piezoelectric film, and the cost of the rigid circuit board is lower. Certainly, the embodiment is also applicable to a flexible circuit board.

In particular, description is made by taking a top side face (as shown in the figures) of the film sheet 21 as a positive electrode 22 of the piezoelectric film, a bottom side face (as shown in the figures) thereof as a negative electrode 23 of the piezoelectric film, one of the exposed pad electrodes on the circuit board 1 that has larger area as a negative electrode 11 of the circuit board, and one of the exposed pad electrodes on the circuit board 1 that has smaller area as a positive electrode 12 of the circuit board. It should also be noted that, in FIG. 3, the thicknesses of the piezoelectric film, the circuit board and the conductive adhesives are deliberately increased in order to clearly present the structure provided by this embodiment, and thus the conductive adhesives are not depicted as being connected to the positive electrode 12 of the circuit board.

The circuit board 1 has a length that is greater than the length of the piezoelectric film 2, the positive electrode 12 of the circuit board is located at one end that is not covered by the piezoelectric film 2, and the negative electrode 11 of the circuit board is bonded to the negative electrode 23 of the piezoelectric film via one three-direction conductive adhesive or z-direction conductive adhesive 31 that has a corresponding shape. One three-direction conductive adhesive 32, the length of which is greater than that of the piezoelectric film 2, is attached to the positive electrode 22 of the piezoelectric film, and a part of the conductive adhesive that extends beyond the piezoelectric film 2 is exactly bonded to the positive electrode 12 of the circuit board below, so as to realize an electrical connection between the positive electrode 22 of the piezoelectric film and the positive electrode 12 of the circuit board.

In addition, the conductive adhesive 32 on the top side face of the piezoelectric film 2 is spaced apart from the positive electrode 12 of the circuit board by the thickness of one conductive adhesive 31 and the piezoelectric film 2. Therefore, in order to obtain a smoother transition at a bonding edge, the length of the film sheet 21 is slightly greater than the length of the conductive adhesive 31 bonded to a negative electrode, so that the transition of a bonding position between one side of the positive electrode 12 of the circuit board that is close to the negative electrode and the conductive adhesive 32 would become much smoother, thereby ensuring high sensing accuracy of the piezoelectric film.

Finally, in order to protect the piezoelectric film, one protective film is generally provided on the top side face of the piezoelectric film.

Embodiment III

Figure 5:
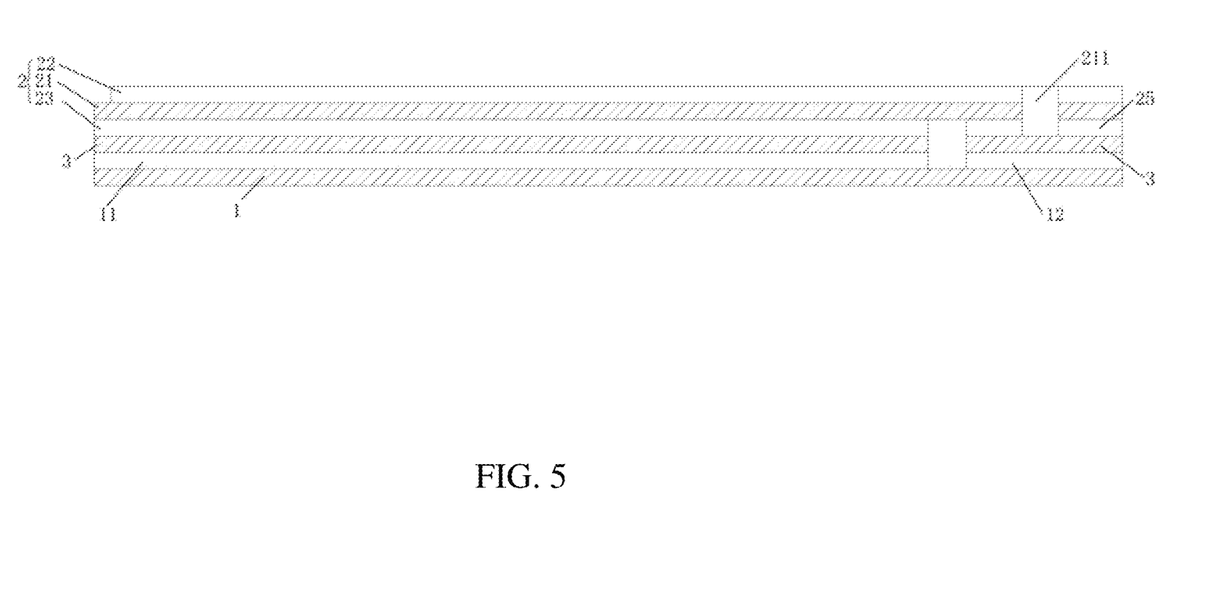
FIG. 5 is a schematic structural diagram of one implementation of Embodiment III of the disclosure.
Figure 6:
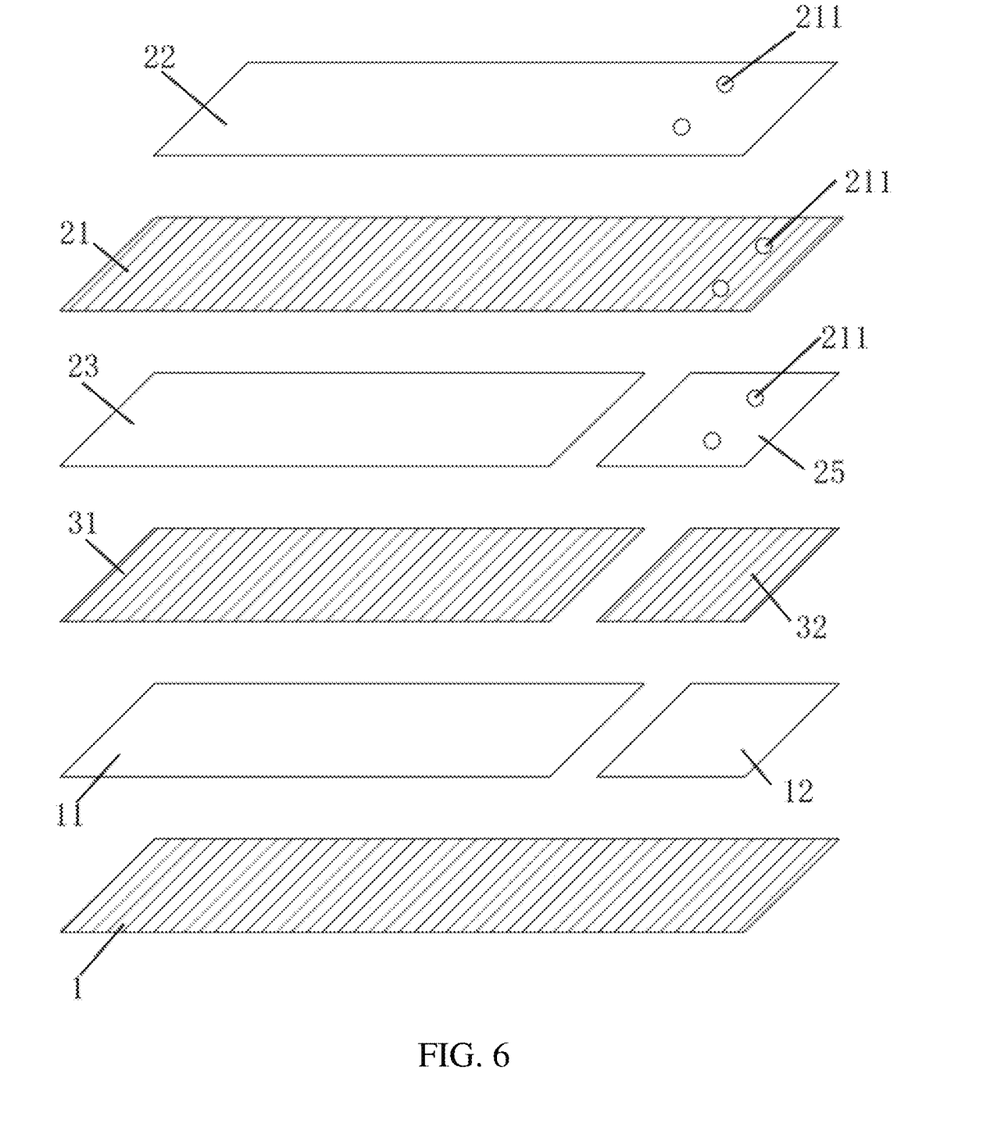
FIG. 6 is a schematic exploded structural diagram of one implementation of the Embodiment III of the disclosure.

As shown in FIGS. 5-6, a transduction unit of a non-contact human sleep physiological parameter detection sensor includes a piezoelectric film, a circuit board 1, which is provided with exposed pad electrodes matching the piezoelectric film, and conductive adhesives. The piezoelectric film 2 includes a film sheet 21 and two electrodes, which are respectively arranged on two side faces of the film sheet 21. The two electrodes cannot both extend to an edge from a same end on the film sheet, so as to prevent the two electrodes from coming into contact at the edge of the film sheet and causing a short circuit. The exposed pad electrodes each adopt a plating with good conductivity and oxidation resistance, and can be manufactured in a leveling process, such as a metal deposition process. The piezoelectric film 2 is attached to the circuit board 1. The two electrodes of the piezoelectric film 2 are respectively connected to the two electrodes on the circuit board 1 via the conductive adhesives. The circuit board 1 can be a rigid circuit board, for example, a conventional PCB taking FR4 as a base material. The conventional rigid circuit board itself also has a certain magnitude of deformation, which can satisfy a sensing range of the piezoelectric film, and the cost of the rigid circuit board is lower. Certainly, the embodiment is also applicable to a flexible circuit board.

In particular, description is made by taking a top side face (as shown in the figures) of the film sheet 21 as a positive electrode 22 of the piezoelectric film, a bottom side face (as shown in the figures) thereof as a negative electrode 23 of the piezoelectric film, one of the exposed pad electrodes on the circuit board 1 that has larger area as a negative electrode 11 of the circuit board, and one of the exposed pad electrodes on the circuit board 1 that has smaller area as a positive electrode 12 of the circuit board.

Figure 7:
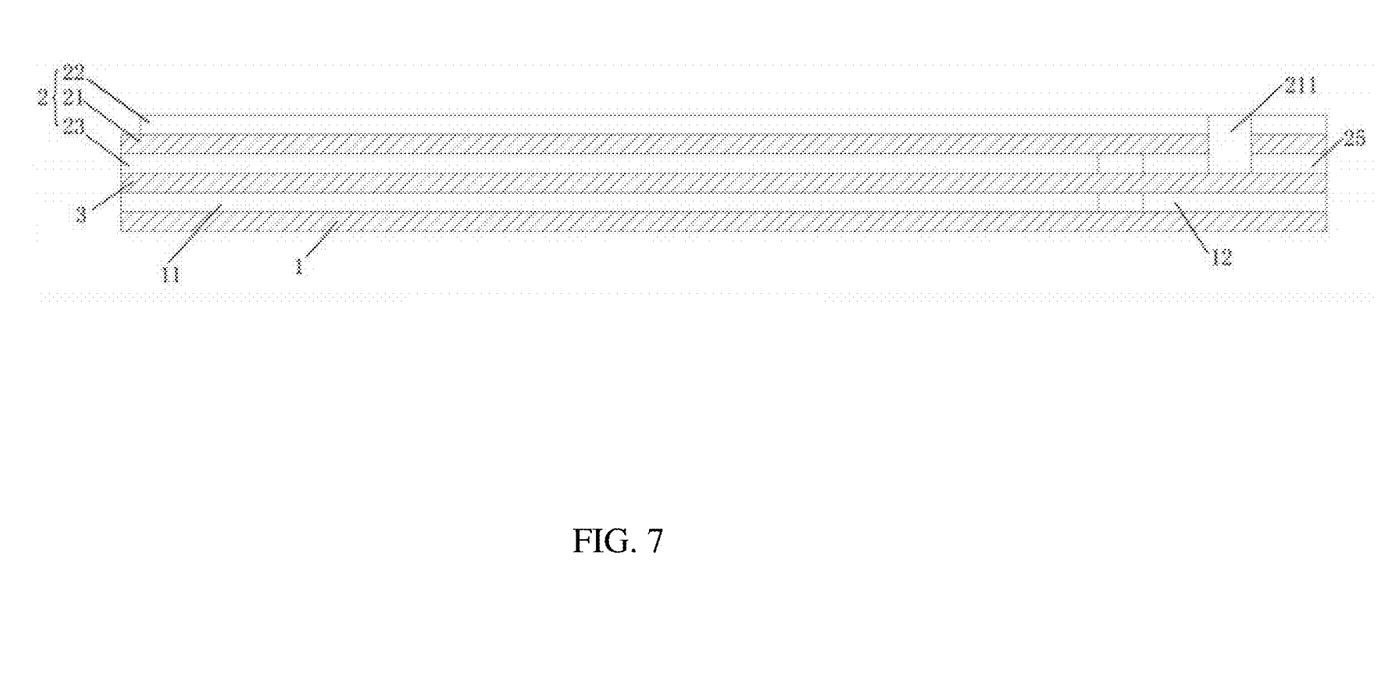
FIG. 7 is a schematic structural diagram of another implementation of the Embodiment III of the disclosure.
Figure 8:
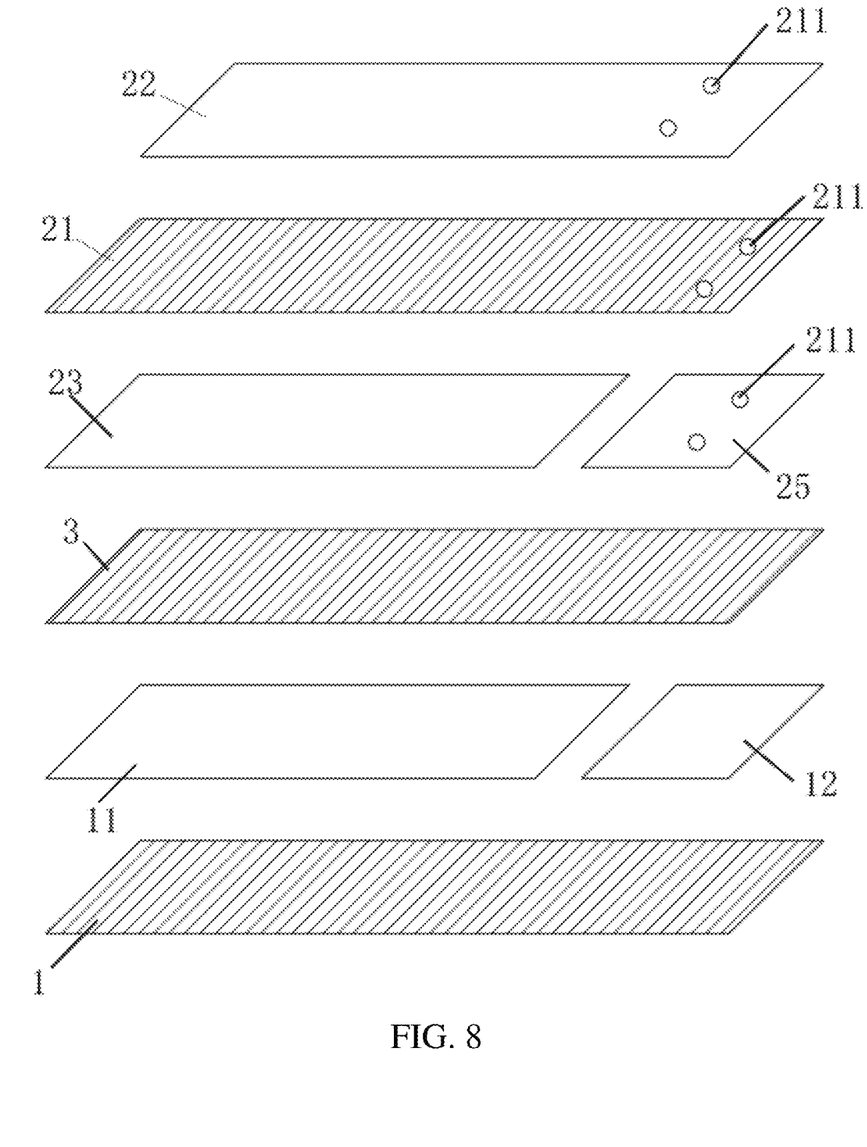
FIG. 8 is a schematic exploded structural diagram of another implementation of the Embodiment III of the disclosure.

On the bottom side face of the film sheet 21, an extension electrode 25 is arranged adjacent to the negative electrode 23 of the piezoelectric film, and on the top side face of the film sheet 21, the positive electrode 22 of the piezoelectric film covers this side that faces away from the extension electrode 25. A through hole 211 penetrates the positive electrode 22 of the piezoelectric film, the film sheet 21 and the extension electrode 25. The extension electrode 25 is electrically connected to the positive electrode 22 of the piezoelectric film through the through hole 211 in such a way that an electrical connection can be established by injecting a conductive adhesive into the through hole 211, by providing a copper sheet or by electroplating an edge, etc. Then, the negative electrode 11 of the circuit board is connected to the negative electrode 23 of the piezoelectric film, and the positive electrode 12 of the circuit board is connected to the extension electrode 25, respectively by using the two three-direction conductive adhesives or z-direction conductive adhesives 31, 32 as shown in FIGS. 5 and 6. Alternatively, the negative electrode 11 of the circuit board is connected to the negative electrode 23 of the piezoelectric film, and the positive electrode 12 of the circuit board is connected to the extension electrode 25, by using the one z-direction conductive adhesive 3 as shown in FIGS. 7 and 8.

Finally, in order to protect the piezoelectric film, one protective film is generally provided on the top side face of the piezoelectric film.

The above description only relates to a preferred implementation of the disclosure, the implementation is one implementation based on the overall concept of the disclosure, but the scope of the disclosure is not limited thereto. Any change or substitution that may be easily conceived by those skilled in the art within the technical scope disclosed by the disclosure shall fall within the scope of the disclosure. Therefore, the scope of the disclosure shall be defined solely by the attached claims.

The invention claimed is:

1. A transduction unit of a non-contact human sleep physiological parameter detection sensor, comprising a circuit board, a piezoelectric film and conductive adhesives, characterized in that the piezoelectric film comprises a film sheet and two electrodes, which are respectively arranged on two side faces of the film sheet; the piezoelectric film is attached to the circuit board; and the two electrodes of the piezoelectric film are respectively electrically connected to two exposed pad electrodes on the circuit board via the conductive adhesives;

one of the electrodes of the piezoelectric film that faces towards the circuit board is connected to one of the exposed pad electrodes on the circuit board via one of the conductive adhesives; one of the side faces of the film sheet that faces towards the circuit board is further provided with a transfer electrode; and another of the conductive adhesives is connected, at its one end, to the transfer electrode and another of the exposed pad electrodes on the circuit board, and is folded, at its opposite end, to another of the side faces of the film sheet through an edge of the film sheet, so as to be connected to the electrode on the another side face.

2. The transduction unit of a non-contact human sleep physiological parameter detection sensor according to claim 1, characterized in that the one conductive adhesive is a three-direction conductive adhesive or a z-direction conductive adhesive, and the another conductive adhesive is a three-direction conductive adhesive.

3. The transduction unit of a non-contact human sleep physiological parameter detection sensor according to claim 1, characterized in that the circuit board has a length greater than that of the piezoelectric film; one of the exposed pad electrodes on the circuit board is arranged outside a coverage face of the piezoelectric film; and one of the conductive adhesives is connected, with its two side faces, to one of the electrodes of the piezoelectric film that faces towards the circuit board, and one of the exposed pad electrodes on the circuit board, respectively, and another of the conductive adhesives is connected, with a same side face, to one of the electrodes of the piezoelectric film that faces away from the circuit board, and another of the exposed pad electrodes on the circuit board.

4. The transduction unit of a non-contact human sleep physiological parameter detection sensor according to claim 3, characterized in that the one conductive adhesive is a three-direction conductive adhesive or a z-direction conductive adhesive, and the another conductive adhesive is a three-direction conductive adhesive.

5. The transduction unit of a non-contact human sleep physiological parameter detection sensor according to claim 1, characterized in that one of the side faces of the film sheet that faces towards the circuit board is further provided with an extension electrode; a through hole penetrates one of the electrodes of the piezoelectric film that faces away from the circuit board, the film sheet and the extension electrode; the extension electrode is connected, through the through hole, to one of the electrodes of the piezoelectric film on a side facing away from the circuit board; and one of the electrodes of the piezoelectric film that faces towards the circuit board, and the extension electrode are respectively connected to the two exposed pad electrodes on the circuit board via the conductive adhesives.

6. The transduction unit of a non-contact human sleep physiological parameter detection sensor according to claim 5, characterized in that the conductive adhesives are formed as one z-direction conductive adhesive, or two z-direction conductive adhesives or three-direction conductive adhesives, which are separated from each other.

7. The transduction unit of a non-contact human sleep physiological parameter detection sensor according to claim 1, characterized in that a side of the piezoelectric film that faces away from the circuit board is further provided with a protective film.

* * * * *